(12) United States Patent
Stuebe et al.

(10) Patent No.: US 7,493,158 B2
(45) Date of Patent: Feb. 17, 2009

(54) ESOPHAGEAL FUNCTION DISPLAY AND PLAYBACK SYSTEM AND METHOD FOR DISPLAYING ESOPHAGEAL FUNCTION

(75) Inventors: Thomas D. Stuebe, Littleton, CO (US); Timothy Paul Stewart, Highlands Ranch, CO (US); Lisa Roos Stewart, Highlands Ranch, CO (US)

(73) Assignee: Sandhill Scientific, Inc., Highlands Ranch, CO (US)

( * ) Notice: Subject to any disclaimer, the term of this patent is extended or adjusted under 35 U.S.C. 154(b) by 0 days.

(21) Appl. No.: 10/935,898

(22) Filed: Sep. 7, 2004

(65) Prior Publication Data
US 2005/0065450 A1      Mar. 24, 2005

Related U.S. Application Data (60) Provisional application No. 60/500,486, filed on Sep. 5, 2003, provisional application No. 60/500,555, filed on Sep. 5, 2003, provisional application No. 60/554,794, filed on Mar. 19, 2004.

(51) Int. Cl.
*A61B 5/05* (2006.01)
*A61B 5/103* (2006.01)
*A61B 5/117* (2006.01)

(52) U.S. Cl. .................. 600/547; 600/587; 600/590; 600/593

(58) Field of Classification Search .................. 600/547, 600/587, 590, 593
See application file for complete search history.

(56) References Cited

U.S. PATENT DOCUMENTS 5,833,625 A * 11/1998 Essen-Moller ............... 600/547
6,132,372 A * 10/2000 Essen-Moller ............... 600/431

* cited by examiner

*Primary Examiner*—Max Hindenburg
*Assistant Examiner*—Jeffrey G Hoekstra
(74) *Attorney, Agent, or Firm*—Cochran Freund & Young; James R. Young (57) ABSTRACT

A system and method for displaying an esophageal operation includes a display device, an interface capable of receiving esophageal impedance and pressure measurements, and a processing system in communication with the display device, the interface, and an esophageal operation model. The processing system is configured to receive a plurality of impedance values from a first plurality of spaced-apart esophageal locations, receive a plurality of pressure values from a second plurality of spaced-apart esophageal locations, process the plurality of impedance values and the plurality of pressure values with the esophageal operation model, display the plurality of impedance values on the display device as a bolus transit, and display the plurality of pressure values on the display device as operational esophagus movement.

30 Claims, 6 Drawing Sheets

FIG 6A

ESOPHAGEAL FUNCTION DISPLAY AND PLAYBACK SYSTEM AND METHOD FOR DISPLAYING ESOPHAGEAL FUNCTION

CROSS REFERENCE TO RELATED APPLICATIONS

This application claims the benefit of U.S. Provisional Patent Application 60/500,486 entitled "Esophageal Function Display And Playback System And Method For Displaying Esophageal Function", filed Sep. 5, 2003, by Thomas D. Stuebe, U.S. Provisional Patent Application 60/500,555 entitled "Esophageal Waveform Analysis for Detection and Quantification of Reflux Episodes", filed Sep. 5, 2003, by Thomas D. Stuebe, and U.S. Provisional Application 60/554, 794 entitled "Intraluminal Impedance: Electromagnetic Modeling, Signal Analysis, and Computer-Assisted Diagnosis of Gastroespohageal Reflux", filed Mar. 19, 2004, by Awad Al-Zaben, Venkatachalam Chandrasekar, and Thomas D. Stuebe, and the entire contents of all of those applications are hereby specifically incorporated by reference herein for all they disclose and teach.

FIELD OF THE INVENTION

The present invention relates generally to medical display systems and more particularly to the display of esophageal functions.

BACKGROUND OF THE INVENTION

Gastrointestinal reflux is the travel of liquids, including stomach acids, up the esophagus. The esophagus normally functions to transport food and liquids down to the stomach during a swallow. During a swallow, a peristaltic wave (i.e., a contraction of the muscles of the esophagus) moves progressively downwardly in the esophagus and pushes the food downwardly during a swallow. In addition, a normal swallowing operation includes a coordinated opening and closing of the Lower Esophageal Sphincter (LES). The LES normally prevents the contents of the stomach from coming back up the esophagus. Therefore, in a normal swallow, the esophageal muscles and the LES work in conjunction to transport a bolus of liquid or food to the stomach and prevent any retrograde travel of the bolus in an opposite direction.

Gastrointestinal reflux, or GastroEsophageal Reflux Disease (GERD), is an abnormal esophageal operation in which a portion of the stomach contents (i.e., a bolus) passes through the LES and travels at least partly back up the esophagus in a retrograde motion. In persons with gastrointestinal reflux, the LES muscle commonly is either weak or relaxes inappropriately with exposure to fatty and spicy foods, certain types of medications, tight clothing, smoking, alcohol consumption, vigorous exercise, or changes in body position. The reflux can cause problems such as heartburn-like pain symptoms, chest pain similar to cardiac problems, aggravated asthma symptoms, hoarseness, sinus problems, snoring problems, and other respiratory problems. Severe or prolonged acid reflux can cause inflammation (esophagitis) and can ultimately damage the lining of the esophagus. Reflux is usually not noticeable or harmful during the day since the esophagus is protected during waking hours by swallowing, by the flow of saliva, and by gravity (assuming the sufferer is standing or sitting up). However, at night, these protective mechanisms are less effective. Consequently, nighttime acid reflux is more likely to remain in the esophagus longer and can cause greater damage.

A normal course of treatment for non-critical reflux is typically the administration of acid-reducing or acid-blocking medications. However, serious and/or long-term gastrointestinal reflux can often necessitate surgery on the LES or on the stomach. Therefore, it is desirable in all cases to be able to detect, measure and diagnose any abnormal operations of the esophagus in order to prevent or treat the reflux.

The occurrence of gastrointestinal reflux has previously been detected by inserting a probe into the esophagus of a subject and measuring acid or pH levels. Therefore, reflux was detected by simply detecting the presence of acid. The drawback of this approach is that it does not show the operational dynamics of the esophagus, i.e., it does not show muscle movement or LES operation, and cannot determine the underlying cause of the reflux. In addition, this approach may not be able to continuously measure acid levels in a patient over a significant period of time. Furthermore, such an approach may not show the extent of reflux occurrence, since this approach is incapable of detecting the reflux of relatively non-acidic stomach fluids.

Esophageal measurements have typically been presented as raw numbers or line graphs that show values taken over time. Therefore, doctors or medical personnel have to interpret the data in order to obtain meaningful information. For example, the reviewer may have to correlate a swallow operation with a feature of a line graph. This is difficult and time consuming. It is even more difficult if the person analyzing the data has to correlate multiple data readings for the patient. Moreover, in order to detect reflux or other swallowing abnormalities, the subject may have to wear a monitoring device that measures and gathers data over hours or even days. Therefore, the reviewer may have to review and assess a tremendous quantity of data. This leads to inefficiency since a large amount of time is spent in analyzing data. Furthermore, the accuracy of the results can be easily degraded as a consequence of human error in reading, processing, and analyzing the large amounts of data. Also, these large amounts of time increase the cost to the patient in performing these tests.

SUMMARY OF THE INVENTION

The present invention overcomes the disadvantages and limitations of the prior art by providing a system and method for displaying esophageal operation of a subject. The esophageal operation display system comprises a display device, an interface capable of receiving esophageal impedance and pressure measurements, and a processing system in communication with the display device, the interface, and an esophageal operation model. The processing system is configured to receive a plurality of impedance values from a first plurality of spaced-apart esophageal locations, receive a plurality of pressure values from a second plurality of spaced-apart esophageal locations, process the plurality of impedance values and the plurality of pressure values with an esophageal operation model, display the plurality of impedance values on the display device as a bolus transit, and display the plurality of pressure values on the display device as operational esophagus movement.

A method of displaying esophageal operation is also disclosed according to an embodiment of the invention. The method comprises receiving a plurality of impedance values from a first plurality of spaced-apart esophageal locations, receiving a plurality of pressure values from a second plurality of spaced-apart esophageal locations, processing the plurality of impedance values and the plurality of pressure values with an esophageal operation model, displaying the plurality of impedance values as a bolus transit, and displaying the plurality of pressure values as operational esophagus movement.

DETAILED DESCRIPTION

Figure 1:
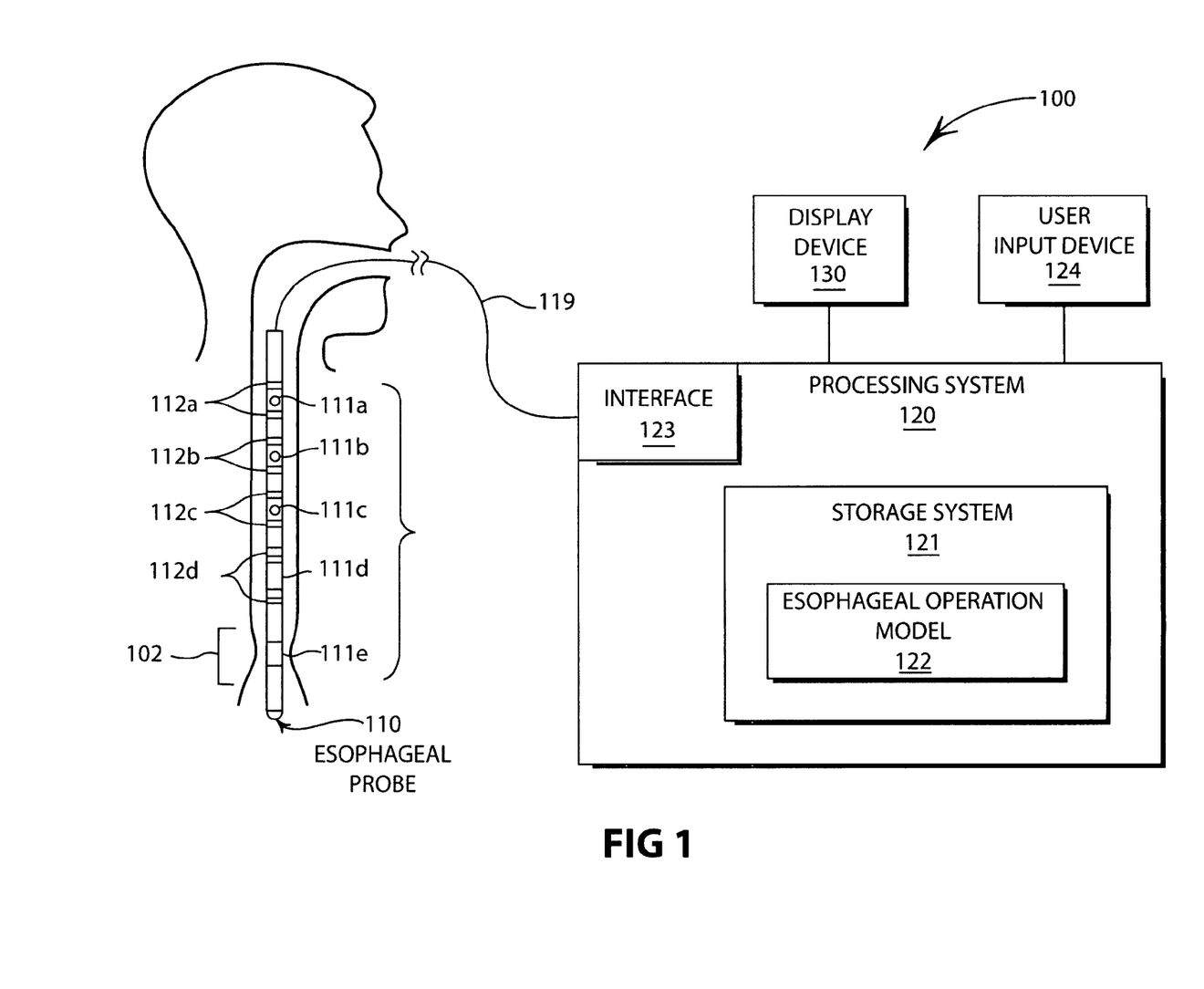
FIG. 1 shows an embodiment of an esophageal operation display system.

FIG. 1 shows one embodiment of an esophageal operation display system 100. The system 100 includes a processing system 120, a display device 130, and an optional user input device 124. The processing system 120 communicates with an esophageal probe 110 and receives impedance and pressure values measured by the esophageal probe 110. In addition, the processing system 120 communicates with the display device 130 and the user input device 124.

The processing system 120 can comprise any desired processing device and includes an interface 123 and a storage system 121 that stores digital data. The processing system 120 receives impedance and pressure values through the interface 123. The storage system 121 stores received impedance and pressure values, and stores other data, including analysis results for impedance and pressure data. In addition, an esophageal operation model 122 is stored in the storage system 121 and is accessed by the processing system 120.

The user input device 124 is in communication with the processing system 120. Through the user input device 124, an operator can initiate and control the analysis of impedance and pressure values and can control the display of esophageal operation results. The user input device 124 can comprise an integral component or can comprise an external device capable of sending inputs and commands to the processing system 120. For example, the user input device 124 can comprise a keyboard or keypad, a mouse, joystick, or other pointing device. Alternatively, the user input device 124 can comprise a general purpose computer configured as a controller, a specialized controller device, an analyzer, a base station, etc. The user input device 124 can also comprise a remote device. The processing system 100 may receive commands from the user input device 124 over a computer network, such as a local area network (LAN), a wide-area network (WAN), the Internet, wirelessly, etc.

The display device 130 can be any type of computer screen or display. It should be understood that the display device 130 may be a component of the processing system 120, or may be a separate device, as in the user input device 124 above. In one embodiment, the processing system 120 is connected to the display device 130 and the user input device 124, by a wire, cable, fiber/optical fiber, etc. In another embodiment, the processing system 120 communicates wirelessly with the display device 130 and the user input device 124, such as through radio frequency (RF) communications, infrared (IR) communications, ultrasonic communications, etc. It should be understood that the display device 130 and the user input device 124 can comprise an integrated user interface, and can comprise a remote computer device that is in communication with the processing system 120, such as through a modem, network card, or other communication interface device (not shown).

In operation, the processing system 120 receives impedance and pressure values, stores the values in the storage system 121 if needed, and accesses the esophageal operation model 122 in order to process the received pressure and impedance values and generate display data. The processing system 120 can receive the impedance and pressure values from the esophageal probe 110, or can receive them from other sources, such as from a storage device or external computer device. The esophageal operation model 122 generates display data from the impedance and pressure values in accordance with processes known to those skilled in the art. The display data can be in a conventional display format, such as an MPEG or other image format, etc. The display data is then processed by processing system 120 and transmitted to and displayed on the display device 130. In addition, the display data can be stored for later use and can be transmitted to other devices. This can enable medical personnel to transfer a patient's data to another person for consultation, etc.

The display of esophageal operation shows a gastroesophageal reflux occurrence, but cannot be identified as acidic unless pH (acidity) measurements are also performed in the esophagus of the subject. To provide direct measurements of the pH values, pH sensors can be added to the probe, as described below. The system and method of the invention will typically be employed when gastroesophageal reflux has been diagnosed, and can advantageously be used to determined the underlying gastroesophageal mechanism responsible for the reflux.

The esophageal operation model 122 describes average or typical characteristics of a human esophagus (or any other animal having an esophagus). The esophageal operation model 122 may include data on, for example, typical esophagus diameter, typical bolus impedances, air impedance, expected food impedances, typical peristaltic pressure, typical resting pressure of the Lower Esophageal Sphincter (LES), typical LES swallowing pressure, correlation of a LES pressure to a LES opening amount, pH, etc. This data is used by the processing system 120 to interpret the received pressure and impedance values, and can be further used to model a peristaltic wave, to model a LES opening and closing operation, to model a bolus transit, etc. Modification of the data and modeling of esophageal operation may employ the processes disclosed in the above referenced applications. Therefore, when the processing system 120 processes the impedance and pressure values with the esophageal operation model 122, the processing system 120 can create the display data that represents the esophageal operation.

The esophageal probe 110 can comprise a combined impedance catheter and manometry (pressure) catheter, or can comprise separate impedance and manometry catheters. The esophageal probe 110 can be substantially flexible or partially rigid, and can include markings or indicia that guide the insertion and the insertion depth of the esophageal probe 110. It should be understood that the drawing is not to scale. The esophageal probe 110 can include pressure sensors 111a-111e that measure pressure values in the esophagus and impedance sensors 112a-112d that measure impedance values. When the esophageal probe 110 is in position, the bottom pressure sensor 111e should be located substantially in the LES 102.

The esophageal probe 110 can be directly connected to the interface 123 of the processing system 120, such as by a wire 119, cable 119, fiber/optical fiber 119, etc. Alternatively, the esophageal probe can include a probe interface (not shown) that is not directly connected to the processing system 120, but can communicate with the processing system 120. In one embodiment, the probe interface communicates with the processing system 120 in a wireless manner, such as through a RF link, an IR link, an ultrasonic link, etc. In another embodiment, the probe interface can include a removable storage medium, such as an optical, magnetic, or solid state storage device, that can store probe measurements and can be transferred to the interface 123 of the processing system 120, where the stored values are downloaded.

It can be seen that the various pressure and impedance sensors are spaced along the length of the esophageal probe 110 in order to obtain impedance and pressure measurements in a variety of spaced apart locations in the esophagus. For example, in the embodiment shown, the bottom pair of impedance sensors 112*d* and the pressure sensor 111*d* are located about 5 centimeters up from the bottom pressure sensor 111*e*. The second set of impedance sensors 112*c* and the pressure sensor 111*c* are located about 10 centimeters up from the bottom sensor 111*e*, the third set of impedance sensors 112*b* and the pressure sensor 111*b* are located about 15 centimeters up from the bottom sensor, and the fourth set of impedance sensors 112*a* and the pressure sensor 111*a* are located about 20 centimeters up from the bottom sensor.

It should be understood that different spacings may be used and different numbers of impedance and pressure sensors may be used, as desired. The sensors are spaced apart in order to track a peristaltic wave and track a bolus transit through the esophagus. It should be understood that more sensors spaced closer together could provide a higher degree of resolution, if needed.

The impedance sensors 112*a*-112*d* comprise conductive portions, such as metallic rings or ring portions. A very small electrical current is transmitted from one contact of an impedance sensor pair and received at the other contact. For example, the top two conductive strips 112*a* can measure an electrical impedance therebetween by transmitting and receiving a small electrical current. However, each impedance sensor pair must be spaced far enough from the other impedance sensors so that the sensors do not receive any stray electrical current from other sensor pairs.

The ratio of voltage to an alternating current for a particular frequency is a measure of the impedance. In practice, impedance is obtained by applying a very small voltage between adjacent contacts of the sensor pair and measuring the resulting electrical current. The highest electrical current flows when there is a bolus present. Impedance is therefore a measure of the specific conductivity of any material adjacent to and in contact with the impedance sensor pairs. Impedance can also provide an indication of the amount of material of the bolus. In one embodiment, the excitation current present between any two impedance sensor contacts is passively limited to less than 8 microamperes, with a frequency of between one and two kilohertz. Other values can be used, depending on the material of the bolus, and the previous values are given merely for purposes of illustration. An excitation current of 8 microamperes is three orders of magnitude below the threshold of cardiac stimulation for a one-kilogram body, and provides an injected power of about 0.00025 microwatts. In one embodiment, the excitation current path is constrained to terminate on an electrode pair by a transformer, and there is no possible current path through other organs.

Figure 3:
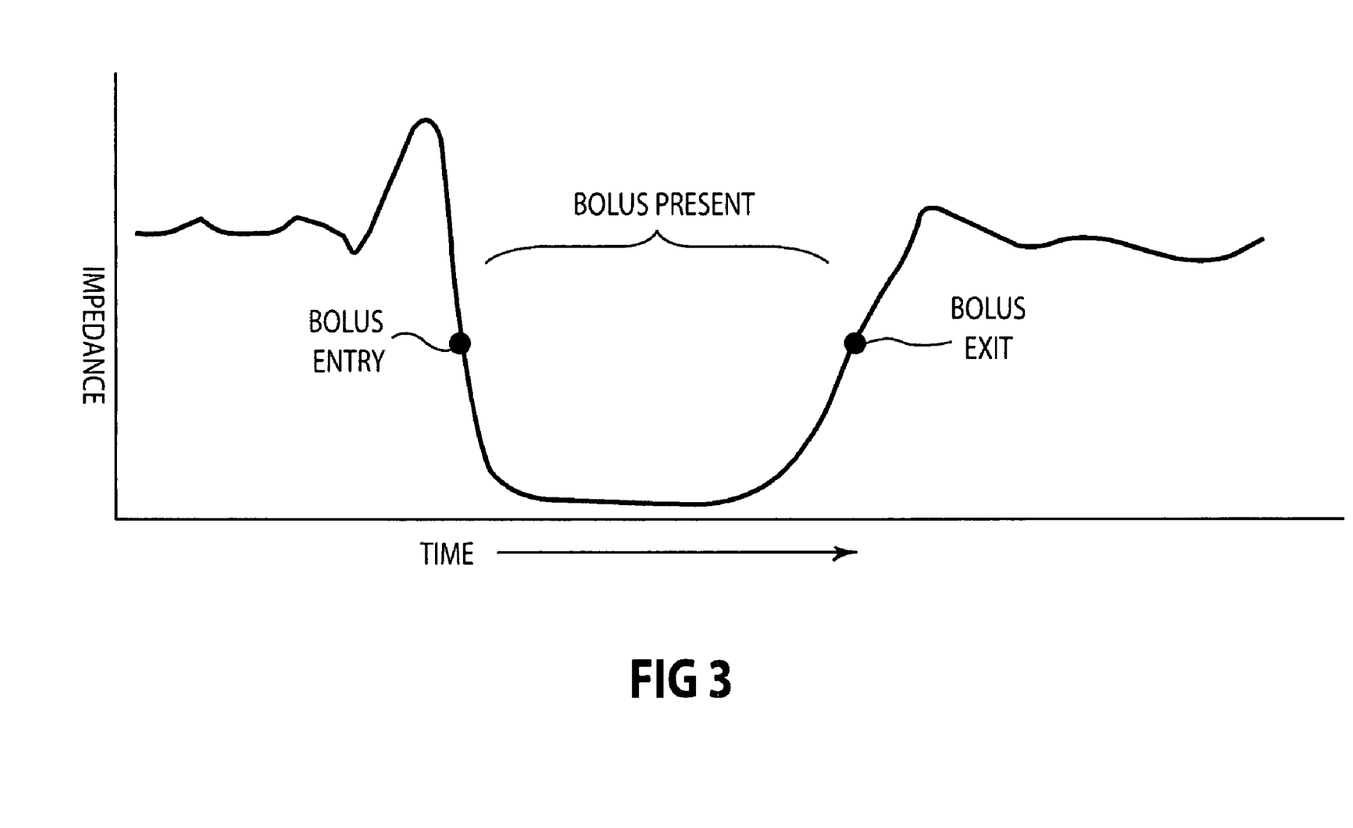
FIG. 3 shows a graph of measured impedance values versus time.

Impedance measurements provide a method for the detection of the bolus head and the bolus tail based upon the response of the impedance signal (see FIG. 3). The impedance values can be used to make several determinations. The impedance values can be used to determine the amount of time that a bolus is present in the esophagus, including the amount of time the bolus is present at each respective level of the esophagus. In addition, the impedance values can be used to determine a bolus transit time, i.e., an amount of time from bolus entry into the proximal esophagus (about 19 centimeters above the LES 102 in a typical person) to bolus exit in the distal esophagus (about 5 centimeters above the LES 102). Furthermore, the impedance values can be used to determine bolus transit effectiveness, i.e., a determination of the ability of the esophagus to achieve bolus transit for each respective test swallow.

The pressure sensors 111*a*-111*e* comprise any suitable pressure sensors, such as described in the above referenced applications. The pressure values measured by the pressure sensors 111*a*-111*d* may be measured as a result of a bolus traveling through the esophagus. The pressure value measured by the bottom pressure sensor 111*e* reflects a pressure exerted by the LES 102.

It should be noted that pressure sensors 111*d* and 111*e* may physically differ from pressure sensors 111*a*-111*c*. The larger size of the bottom pressure sensor 111*e* will better accommodate the need to capture LES readings and will accommodate some variance in placement of the probe 110 (i.e., each subject may have a different length esophagus). The larger size of the pressure sensor 111*d* allow pressure sensor 111*d* to obtain a more accurate reading in the esophagus near the LES 102, due to the higher likelihood of reflux in this region. In one embodiment, the pressure sensors 111*d*-111*e* may be circumferential sensors that measure pressure on the circumference of the esophageal probe 110, while the pressure sensors 111*a*-111*c* can comprise spot sensors that measure pressure at a specific region of the esophageal probe 110, such as a pressure sensor having a circular face.

Figure 2:
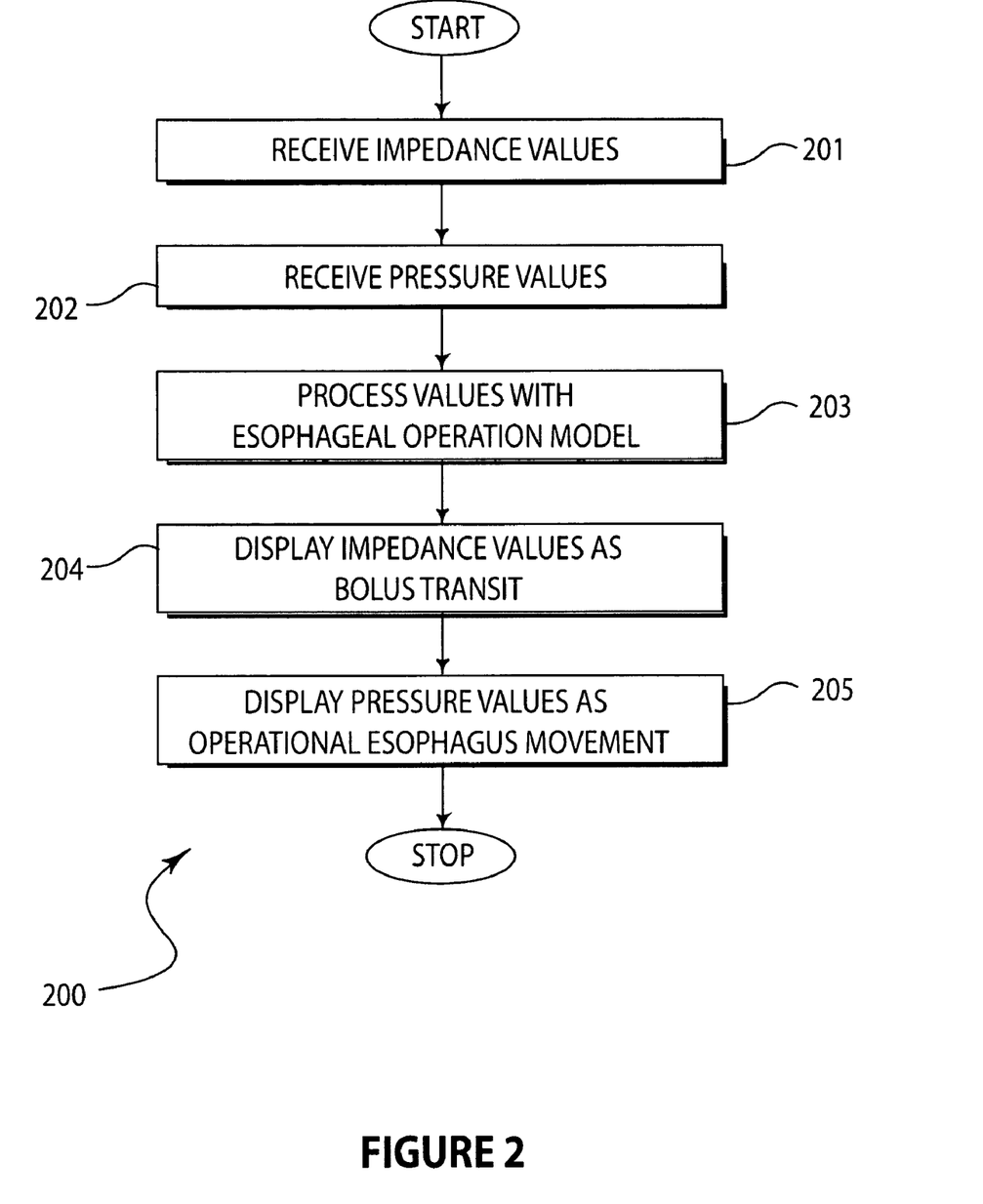
FIG. 2 is a flowchart of a method of displaying esophageal operation according to an embodiment of the invention.

FIG. 2 is a flowchart 200 of a method of displaying esophageal operation according to an embodiment of the invention. In step 201, the processing system 120 receives a plurality of impedance values, such as a set of time-sampled impedance values from a plurality of spaced-apart esophageal locations. In one embodiment, the plurality of impedance values are received from the esophageal probe 110. The impedance values can be accumulated, stored, recalled, etc., as disclosed above.

In step 202, the processing system 120 receives a plurality of pressure values, such as a set of time-sampled pressure values from a plurality of spaced-apart esophageal locations. The plurality of pressure values can be received directly from the esophageal probe 110 or retrieved from storage for processing and display. The pressure values can be stored, accumulated, processed, recalled, etc. for subsequent display on the display device, or the processed data can be stored for subsequent display on the display device. In one embodiment the spaced-apart locations of the impedance and pressure values are substantially the same, although in other embodiments, the pressure and impedance values could be obtained at different, non-corresponding locations in the esophagus.

The impedance and pressure values are typically received from the esophageal probe 110 during or after a measurement session. The processing system 120 can accumulate the values. The measurement session can include specific swallowing and postural procedures performed by the test subject, including swallowing a test bolus of a fluid having known and controlled properties (such as viscosity). The test bolus may therefore exercise the dynamic muscular operation of the esophagus. The measurement session can be conducted in order to ascertain peristaltic wave strength, peristaltic wave speed/contraction timing, bolus transit effectiveness, and bolus transit timing. The subject's performance can be analyzed and compared to normal values in order to determine a disease state and to plan any indicated therapy.

In step 203, the processing system 120 processes the impedance and pressure values with the esophageal operation model 122, as previously discussed. The processing is performed in order to generate display data representative of the esophageal operation.

In step 204, the processed impedance values are displayed on a graphical display, such as on the display device 130. The processed impedance values represent the location and the movement of a bolus (i.e., a bolus transit). In addition, the processed impedance values can be used whether the bolus comprises water, acid, food or food liquids, or even air.

In step 205, the processed pressure values are displayed as operational esophagus movement. For example, the processed pressure values can represent a peristaltic wave and opening and/or closing of the LES 102. Therefore, the processed pressure values are displayed as muscular movements within the esophagus. The pressure values can be used to determine proper peristaltic wave behavior. For example, if the contraction pressure of the peristaltic wave is greater than or equal to about 30 mmHg and the speed of the wave is about 8.0 centimeters per second, the doctor may determine that the peristalsis was effective.

FIG. 3 shows a graph of measured impedance values versus time. The graph shows how the impedance values may vary during transit of a bolus. For example, if the bolus is a fluid, the measured impedance will normally drop due to the presence of the water around the impedance probe 110, and consequently the bolus can be detected over time by the trough of impedance values. In addition, the chart may be used to determine a bolus exit from the esophagus (if there is one).

Figure 4:
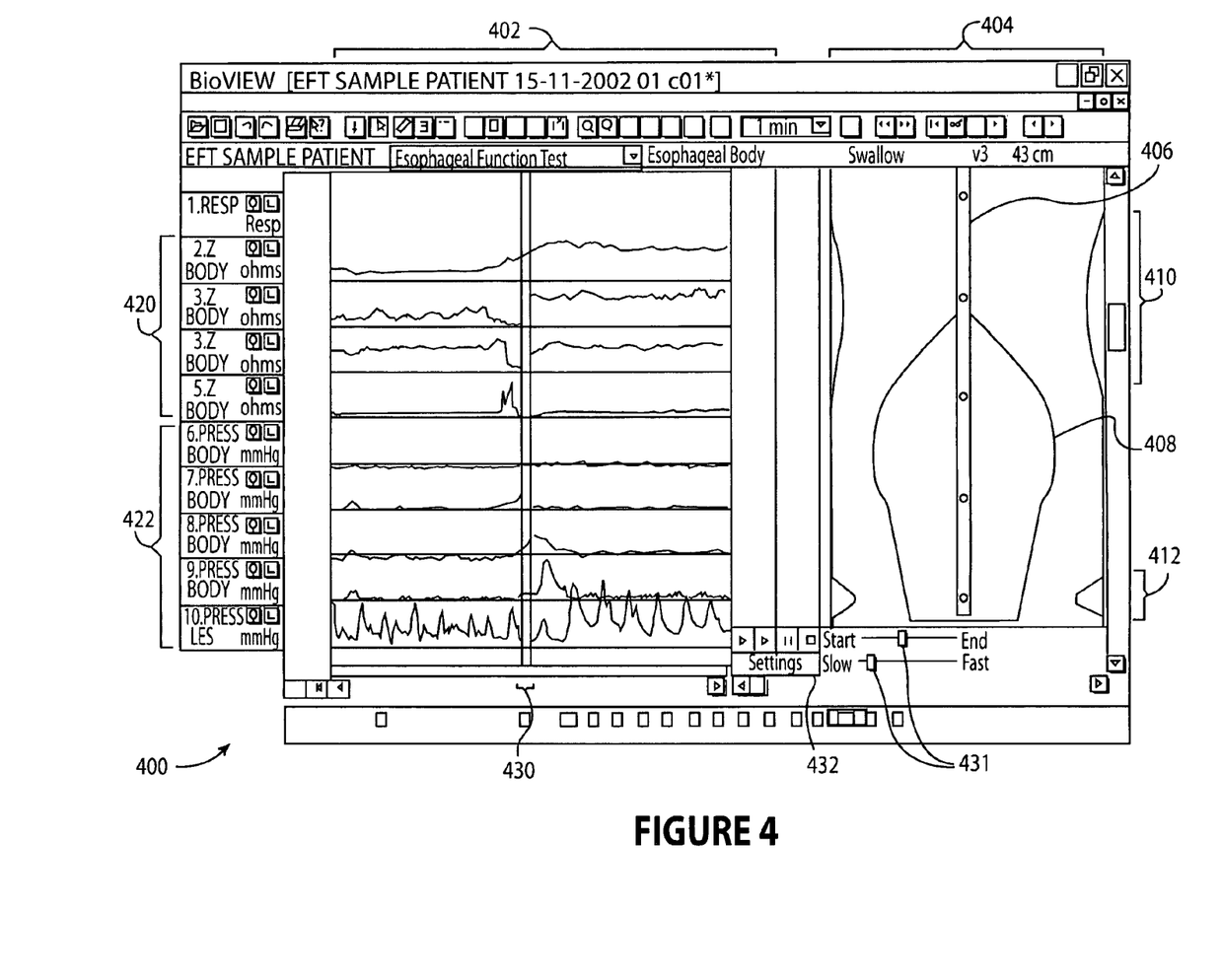
FIG. 4 shows an esophageal operation display screen according to an embodiment of the invention.

FIG. 4 shows an esophageal operation display screen 400 according to an embodiment of this invention. The screen 400 comprises display data that is viewed on the display device 130 (see FIG. 1). The screen 400 includes a data display portion 402 and an animated display portion 404. It can be seen from FIG. 4 that multiple time-sampled impedance values (i.e., impedance traces 420) and multiple time-sampled pressure values (i.e., pressure traces 422) are simultaneously displayed. It should be understood that the data and animated displays can be provided in other formats and can include different user interface icons, buttons, text and/or labels, etc. Through use of the screen 400, the invention advantageously provides a visual representation of both the bolus transit and the esophageal operation.

The data display portion 402 can include the display of a line graph for each impedance and pressure sensor of the esophageal probe 110. The line graphs show measured esophageal values over a window of time. The data display portion 402 can include impedance traces 420 (displayed in terms of impedance Z in units of ohms) and pressure traces 422 (in units of millimeters of mercury, or mmHg). In one embodiment, a user can select a time window (such as a time window for viewing in the animated display portion 404, using the vertical window control boundaries 430), can select time scales, can move chronologically forward or backward through the displayed data, can start and stop a motion of the graphs over time, can halt the graphs at a particular point in time (such as if the user spots an anomaly in the data), can zoom in or out, can select vertical display scaling, can select sensors to be displayed (i.e., the user can add or remove certain sensor values), etc. All of these functions are capable of being provided by those skilled in the art of display technology.

The animated display portion 404 can be animation drawings or other representation of esophageal operation. The animated display portion 404 represents pressure values as esophageal muscle action and represents impedance values as bolus transit. It should be noted that the animated display of the bolus does not necessarily represent an actual bolus volume. The animated display portion 404 can include a probe representation 406 of the esophageal probe 110, including depicting the impedance and pressure sensor locations. The animated display portion 404 can include a black-and-white, grayscale, or color animation. The animated display portion 404 can additionally display the acidity of the bolus, such as by using a color scale, if acidity measurements from pH sensors on the probe 110 are received along with the impedance and pressure values.

The animated display portion 404 can be displayed in real time or can be displayed according to a user-selected time scale. For example, the user can control the animation using the start/end and slow/fast controls 431. The user can further use the playback controls 432 to control the animated display portion 404. Consequently, this invention enables the user to sift through large amounts of data very quickly and efficiently and to look for specific actions of the esophagus, and it can repeatedly loop through a specific portion of data for repetitive viewing by the user. In this manner, the user can look for certain abnormalities visually, such as the peristaltic wave 410 passing the bolus 408, the LES 412 not returning to a closed position after a bolus transit, the LES 412 not returning to a closed position within a certain amount of time, movement of the LES 412 without an accompanying peristaltic wave and/or bolus, etc.

The animated display portion 404 advantageously allows a doctor, a medical technician, and/or the patient to view and understand the operation of a particular patient's esophagus, and further enables efficient and intuitive understanding of any abnormal esophageal operation by visual observation. For example, the viewer can observe a peristaltic wave 410 in conjunction with the opening/closing of the LES 412. The user can see the peristaltic wave 410 move down the esophagus and can see the bolus 408 in relation to the peristaltic wave 410. In addition, the viewer can observe the opening and closing of the LES 412 in relation to both the peristaltic wave 410 and the transit of the bolus 408.

The advantages of the animated display portion 404 are further evident when compared to the data display portion 402. The series of line graphs of the data display portion 402, although they contain the same information as the animated display portion 404, are more difficult to interpret, even for trained medical personnel, than the animated display 404. For example, the peaks and valleys in the various line graphs are hard to relate to an actual physical function of the esophagus, whereas the animated display 404 shows such physical functions visually. In addition, without the animated display 404, the viewer must mentally correlate the pressure and impedance values and how these values represent esophageal physical movements, functions, and abnormalities. Moreover, the animated display 404 may help the user to detect important esophageal abnormalities that may otherwise be missed by the user, especially in light of the amount of data, which is typically obtained over a long study period, for example, 24 hours. Hence, the animated display helps the person analyzing the data to view a visual representation of the data, which allows large amounts of data to be analyzed in a quick and easy manner.

Figure 5A:
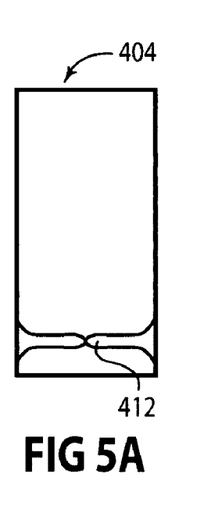
FIGS. 5A-5E illustrate a normal swallow sequence as shown on an animated display portion of the esophageal operation display system.
Figure 5B:
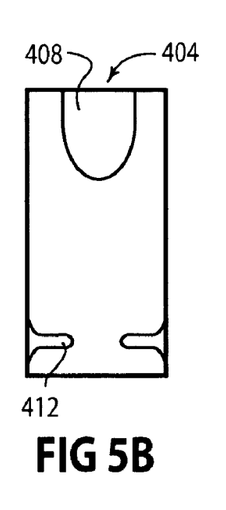
Figure 5C:
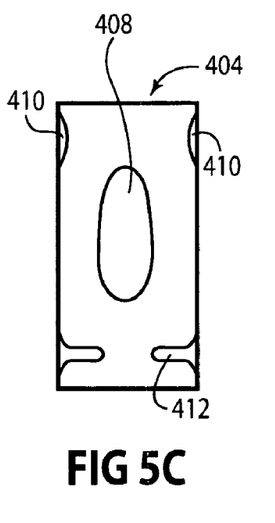
Figure 5D:
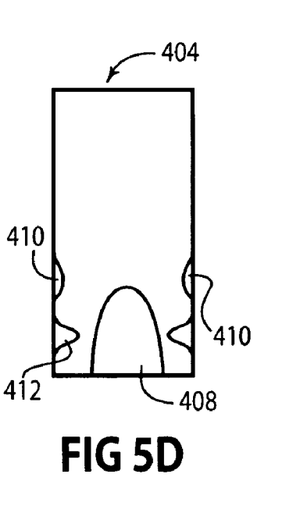
Figure 5E:
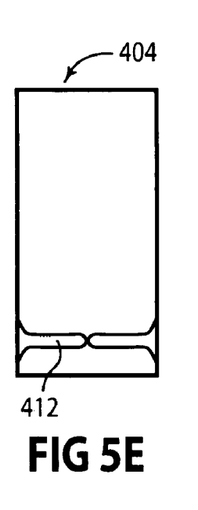

FIGS. 5A-5E illustrate a normal swallow sequence as shown on the animated display portion 404 of the esophageal operation display system 100. FIG. 5A depicts the esophagus at rest, wherein the LES 412 is basically closed and the rest of the esophagus is relaxed. FIG. 5B shows the LES 412 starting to open and also shows the presence of the bolus 408 in the esophagus. FIG. 5C shows the esophagus when the bolus 408 has moved closer to the LES 412, and further shows the peristaltic wave 410 following the bolus 408. This is expected and normal esophageal operation, wherein the peristaltic wave 410 (i.e., the rippling contraction of the esophageal muscles) follows the bolus 408 and forces it down the esophagus. FIG. 5D shows the bolus 408 passing through the open LES 412, with the peristaltic wave 410 immediately behind it. FIG. 5E shows the esophagus after the bolus 408 has passed into the stomach and the LES 412 has returned to a closed position. The peristaltic wave 410 has terminated, and thus cannot be seen in FIG. 5E.

Figure 6A:
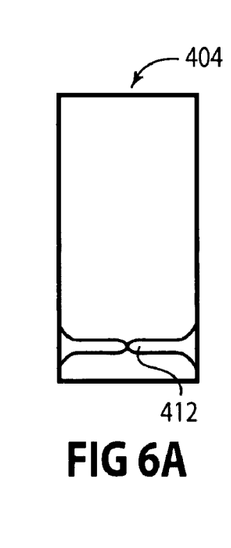
FIGS. 6A-6E illustrate an abnormal swallow sequence as shown on the animated display portion.
Figure 6B:
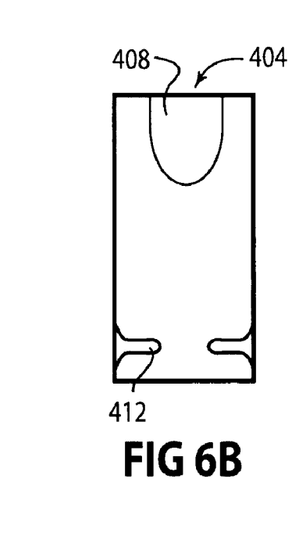
Figure 6C:
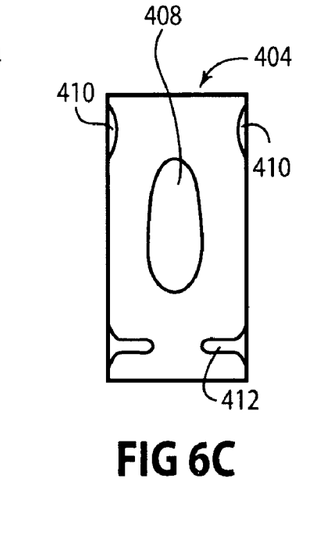
Figures 6D, 6E:
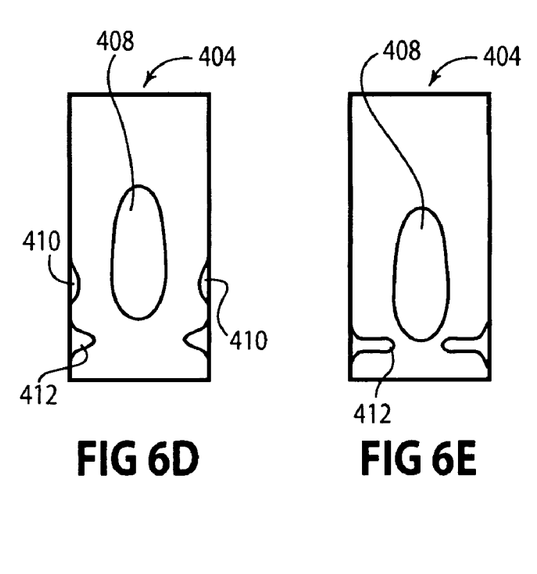

FIGS. 6A-6E illustrate an abnormal swallow sequence as shown on the animated display portion 404. It should be understood that there are other types of abnormal swallow sequences, and this sequence shows just one mechanism. Other mechanisms may likewise be shown and depicted by the invention. FIG. 6A again shows the esophagus at rest, with the LES 412 being closed. FIG. 6B again shows the bolus 408 approaching the LES 412, which is starting to open. FIG. 6C again shows the bolus 408 approaching the LES 412 followed by the peristaltic wave 410. FIG. 6D shows a deviation wherein the LES 412 has not fully opened, and consequently the peristaltic wave 410 passes the bolus 408. As a result, in FIG. 6E the bolus 408 has not passed through the LES 412 and is still within the esophagus, even though the peristaltic wave 410 has terminated. Therefore, in this example, the swallowing is abnormal and has not successfully completed.

It should be understood that an abnormal swallow sequence may include other problems. For example, an abnormal swallow sequence may be indicated by an incomplete opening of the LES 412, a poor or ineffective peristaltic wave 410, or a failure of the LES 412 to fully close (wherein a bolus actually emerges from the stomach and moves upward in a retrograde motion and is not contained by the LES 412).

The invention provides a graphical representation of esophageal function and provides a two-dimensional animated representation of dynamic esophageal operational. The invention also provides swallow and reflux data in real time, allowing changes to the time scale, stopping and starting of the display of esophageal operation, and the ability to focus on critical swallowing operations.

The invention provides several benefits. The invention enables pressure and impedance values to be processed and displayed together in order to present an accurate and life-like model of swallowing operations. The invention provides an improved and easily used display of esophageal data, including data that allows medical personnel to fully understand normal and abnormal esophageal operation. The invention provides benefits in training of medical personnel. The invention allows medical personnel to accurately assess and diagnose swallowing abnormalities while reducing data processing and analysis time. The invention can be utilized to efficiently determine a course of treatment for a patient. In addition, the invention enables display of patients' problems/symptoms in order to show the existence of a swallowing abnormality and to explain a swallowing and/or reflux problem. Moreover, a dynamic playback of bolus transit is achieved without use of a radiation scan, with its attendant cost and risk drawbacks.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of displaying a representation of esophageal function of an esophagus that includes a lower esophageal sphincter, comprising:
   receiving a plurality of impedance values detected at a first plurality of spaced-apart esophageal locations over a time period;
   receiving a plurality of pressure values detected at a second plurality of spaced-apart esophageal locations over the time period, at least one of which pressure values is substantially in the lower esophageal sphincter;
   processing said plurality of impedance values and said plurality of pressure values from at least some part of the time period with an esophageal operation model to generate display data representative of bolus transit from the plurality of impedance values in said at least some part of the time period, esophageal movement from the plurality of pressure values in said at least some part of the time period, and lower esophageal sphincter operation from the pressure value in the lower esophageal sphincter in said at least some part of the time period; and
   generating image data from the display data representative of bolus transit, esophageal movement, and lower esophageal sphincter operation for display simultaneously on a display device.

2. The method of claim 1 further comprising simultaneously displaying the bolus transit, esophageal movement, and the lower esophageal sphincter operation together in an animated display of bolus transit and esophageal operation.

3. The method of claim 2 further comprising:
   displaying said plurality of impedance values on said display device as a line graph of the impedance values versus time; and
   displaying said plurality of pressure values on said display device as a line graph of the pressure values versus the same time as the impedance values displayed.

4. The method of claim 1 wherein said image data graphically depicts a swallowing occurrence.

5. The method of claim 1 wherein said image data graphically depicts a gastrointestinal reflux occurrence.

6. The method of claim 1 wherein said plurality of pressure values are representative of swallow pressures exerted on a bolus by esophagus muscles.

7. The method of claim 1 wherein said image data illustrates muscle contraction and muscle expansion patterns of an esophagus.

8. The method of claim 1 wherein said plurality of pressure values includes pressures generated by a lower esophageal sphincter.

9. The method of claim 1 wherein said plurality of pressure values further comprises pressures representative of a peristaltic wave.

10. The method of claim 1 wherein said plurality of impedance values comprises a plurality of time-sampled impedance values.

11. The method of claim 1 wherein said plurality of pressure values further comprises a plurality of time-sampled pressure values.

12. The method of claim 1 wherein said process of generating image data and displaying said image data on said display device is performed as said pressure values and said impedance values are received.

13. The method of claim 12 further comprising:
storing said pressure values and said impedance values for retrieval and display on said display device.

14. The method of claim 13 further comprising:
displaying said image data in accordance with a user selected time scale.

15. The method of claim 14 further comprising:
allowing a user to pause and reverse said image data that is displayed on said display device.

16. A method of displaying a representation of peristalsis and bolus transit in an organ, comprising:
receiving a plurality of impedance values detected at a plurality of longitudinally disposed locations along a portion of the organ during a time period;
receiving a plurality of pressure values detected at a plurality of longitudinally disposed locations along said portion of the organ during the time period;
processing the plurality of impedance values to generate display data that is indicative of bolus transit in the organ during the time period;
processing the plurality of pressure values to generate display data that is indicative of peristalsis of the organ during the time period; and
displaying the bolus transit display data and the peristalsis display data together in a common visual display simultaneously.

17. The method of claim 16, wherein the visual display includes line graphs derived from the impedance values detected along the portion of the organ in the time period and line graphs derived from the pressure values detected along the portion of the organ in the time period.

18. The method of claim 16, wherein the visual display includes a visual representation of the portion of the organ.

19. The method of claim 18, wherein the visual display includes a visual representation of the bolus transit display data and of the peristalsis display data together with the visual representation of the portion of the organ.

20. The method of claim 19, wherein the visual display is animated to represent peristaltic movement and bolus transit in the portion of the organ simultaneously based on the peristalsis display data and the bolus transit display data for at least a portion of said time period.

21. The method of claim 20, including selecting the portion of said time period for the animated visual display.

22. The method of claim 21, including:
displaying line graphs derived from the impedance values detected along the portion of the organ in the time period together in a common display with line graphs derived from the pressure values detected along the portion of the organ in the time period; and
selecting the portion of said time period for the animated visual display from said common display of the impedance value line graphs and pressure value line graphs.

23. A method of displaying a representation of peristalsis in an organ, comprising:
receiving a plurality of pressure values detected at a plurality of longitudinally disposed locations along a portion of the organ during a time period;
processing the plurality of pressure values to generate display data that is indicative of peristalsis of the organ during the time period; and
displaying the peristalsis display data in a visual display that includes a visual representation of the portion of the organ so that peristalsis of the organ indicated by the peristalsis display data is displayed in visual association with the visual representation of the portion of the organ.

24. The method of claim 23, wherein the visual display of the peristalsis is animated to represent peristaltic movement in the portion of the organ based on the peristalsis display data for at least a portion of said time period.

25. The method of claim 24, including selecting the portion of said time period for the animated visual display.

26. The method of claim 25, including:
displaying line graphs derived from the pressure values detected along the portion of the organ in the time period; and
selecting the portion of said time period for the animated visual display from said display of the line graphs.

27. A method of displaying a representation of bolus transit in an organ, comprising:
receiving a plurality of impedance values detected at a plurality of longitudinally disposed locations along a portion of the organ during a time period;
processing the plurality of impedance values to generate display data that is indicative of bolus transit in the organ during the time period; and
displaying the bolus transit display data in a visual display that includes a visual representation of the portion of the organ so that bolus transit in the organ indicated by the bolus transit display data is displayed in visual association with the visual representation of the portion of the organ.

28. The method of claim 27, wherein the visual display of the bolus transit is animated to represent bolus transit in the portion of the organ based on the bolus transit display data for at least a portion of said time period.

29. The method of claim 28, including selecting the portion of said time period for the animated visual display.

30. The method of claim 29, including:
displaying line graphs derived from the impedance values detected along the portion of the organ in the time period; and
selecting the portion of said time period for the animated visual display from said display of the line graphs.

* * * * *